United States Patent
Chang et al.

(10) Patent No.: US 12,251,458 B1
(45) Date of Patent: Mar. 18, 2025

(54) ANTI-AGING PREPARATION FOR SKIN AND APPLICATION THEREOF

(71) Applicant: South China Normal University, Guangdong (CN)

(72) Inventors: Haocai Chang, Guangdong (CN); Wenwen Ouyang, Guangdong (CN); Yongci Tan, Guangdong (CN); Jing Tong, Guangdong (CN)

(73) Assignee: South China Normal University, Guangzhou (CN)

( * ) Notice: Subject to any disclaimer, the term of this patent is extended or adjusted under 35 U.S.C. 154(b) by 0 days.

(21) Appl. No.: 18/923,620

(22) Filed: Oct. 22, 2024

(30) Foreign Application Priority Data

Oct. 25, 2023 (CN) .......................... 202311386845.4

(51) Int. Cl.
*A61K 8/46* (2006.01)
*A61Q 19/08* (2006.01)

(52) U.S. Cl.
CPC ................ *A61K 8/46* (2013.01); *A61Q 19/08* (2013.01)

(58) Field of Classification Search
None
See application file for complete search history.

(56) References Cited

U.S. PATENT DOCUMENTS

| 9,044,427 B2* | 6/2015 | Kumar | A61K 31/10 |
| 9,060,967 B2* | 6/2015 | Maniar | A61K 31/10 |
| 2013/0012588 A1 | 1/2013 | Kumar et al. | |

* cited by examiner

*Primary Examiner* — Brian J Davis

(57) ABSTRACT

The present disclosure relates to the technical field of anti-aging preparations for skin, and especially relates to an anti-aging preparation for skin and an application thereof. Components of the anti-aging preparation for skin includes a 4-[(1E)-2-[[(4-chlorophenyl)methyl]sulfonyl]alkyne]-benzoic acid and/or a salt thereof. In the present disclosure, the anti-aging effect of the 4-[(1E)-2-[[(4-chlorophenyl)methyl]sulfonyl]alkyne]-benzoic acid and the salt thereof (such as sodium 4-[(1E)-2-[[(4-chlorophenyl)methyl]sulfonyl]alkyne]-benzoate) on skin has been discovered, and the 4-[(1E)-2-[[(4-chlorophenyl)methyl]sulfonyl]alkyne]-benzoic acid and the salt thereof can be applied in preparing the anti-aging preparation for skin that has good anti-aging effect on skin.

2 Claims, 4 Drawing Sheets

Specification includes a Sequence Listing.

ANTI-AGING PREPARATION FOR SKIN AND APPLICATION THEREOF

CROSS-REFERENCE TO RELATED APPLICATION

This application claims priority of Chinese Patent Application No. 202311386845.4, filed on Oct. 25, 2023, the entire contents of which are incorporated herein by reference.

TECHNICAL FIELD

The present disclosure relates to the technical field of anti-aging preparations for skin, and especially relates to an anti-aging preparation for skin and an application thereof.

SEQUENCE LISTING

The instant application contains a Sequence Listing with 4 sequences, which has been submitted electronically in XML format and is hereby incorporated herein by reference in its entirety. Said XML copy, created Oct. 21, 2024, is named HBHM-US-1-08-F-Sequence Listings.xml, and is 4.46 bytes.

BACKGROUND

Skin aging refers to the phenomenon of skin decrepitude caused by natural or unnatural factors, and is specifically reflected by rough skin, wrinkles, lack of elasticity, sagging, dryness, and capillary dilation, with wrinkles being an important sign. Fine lines at the corners of eyes, crow's feet, nasolabial folds, neck lines, and facial fine wrinkles are mainly targeted by anti-aging products. The skin is composed of epidermis, basement membrane, dermis, subcutaneous tissue, and skin appendages such as hair follicles, while the internal structure of aged skin undergoes various changes from the epidermis to the dermis. The wrinkle is primarily caused by uneven depressions in the dermis that contains collagen, elastin, and other fibers, and these are the main elements that make the skin smooth and youthful, and form the supportive framework of the skin.

The generation of wrinkles involves multiple factors, such as the long-term accumulation of metabolic waste and toxins in skin, chronic accumulation of ultraviolet (UV) radiation damage, smoking, decreased estrogen, high life pressure, insufficient sleep, and improper skincare techniques, all of which can cause skin aging and wrinkle formation. These factors can directly or indirectly damage the collagen in the dermis, resulting in a decrease in skin elasticity and toughness, so that the skin loses normal supportive structure and elastic retraction, leading to skin sagging. This results in the generation of fine wrinkles, sometimes accompanied by skin thinning, a leather-like appearance, capillary dilation, a dull and glossy appearance, abnormal pigmentation, and even cancerization.

Collagen, the most abundant protein in human body, is primarily found in skin, bones, and blood vessels. Type I collagen, most widely distributed in dermis, accounts for about 85% of the total collagen in the extracellular matrix of skin cells, and intertwines with elastic fibers to support the skin, provide tension and elasticity, and protect the skin. Type I collagen consists of two peptide chains, and has a strong affinity and good moisturizing effect on the skin due to its hydrolysate polypeptide chains containing more hydrophilic groups. The increased content of type I collagen in the dermis can not only remove wrinkles but also whiten and moisturize skin, reduce dark circles and eye bags, and make the skin smooth and glossy. Additionally, type I collagen also plays an important role in organ development, wound healing, and tissue repair.

The loss of collagen mainly leads to skin aging. As people age, the collagen content in the skin decreases by 1% per year, and the ability of fibroblasts to synthesize collagen also declines. Meanwhile, collagen is degraded by matrix metalloproteinases (MMPs), and type I collagen can be cleaved by MMP-13 into fragments that are ¼ and ¾ of its original size. In daily life, factors such as UV radiation can induce MMPs synthesis through various signaling pathways, with the mitogen-activated protein kinase (MAPK) signaling pathway being the primary, and the activated AP-1 in this pathway can promote MMPs synthesis. In addition, MMPs can be activated through the NF-κB signaling pathway, thereby degrading collagen, causing skin sagging, and leading to wrinkle formation.

Up to now, most anti-aging and wrinkle-removing products for skin function by their own moisturizing effect, mainly by increasing the water content of skin and mildly swelling epidermis, thereby reducing fine wrinkles and temporarily minimizing pores. However, it has not been proven that moisturizers can directly delay the aging process. In recent years, various anti-aging and wrinkle-removing products for skin are available in the skincare industry, and promoting the increase of type I collagen content in the skin has been regarded as a promising anti-aging target. So far, a plenty of preparations have been studied and developed to promote the synthesis of type I collagen. For example, retinol, a hot component in the skincare industry, is applied in various anti-aging products for skin due to its proven ability to promote the synthesis of type I collagen, and components such as lapacho extract, *Leonurus japonicus* extract, *Polygonatum odoratum* extract, and Salmo salar roe extract are also gradually being developed. However, there is no public reporting on the application of 4-[(1E)-2-[[(4-chlorophenyl)methyl]sulfonyl]alkyne]-benzoic acid and a salt thereof in skin anti-aging.

SUMMARY

An objective of the present disclosure is to provide an anti-aging preparation for skin and an application thereof, utilizing a 4-[(1E)-2-[[(4-chlorophenyl)methyl]sulfonyl]alkyne]-benzoic acid and/or a salt thereof (such as sodium 4-[(1E)-2-[[(4-chlorophenyl)methyl]sulfonyl]alkyne]-benzoate) to achieve the anti-aging effect on skin.

To achieve the above objective, the present disclosure provides the following technical solutions.

In a first technical solution of the present disclosure, an application of a 4-[(1E)-2-[[(4-chlorophenyl)methyl]sulfonyl]alkyne]-benzoic acid and a salt thereof in preparing an anti-aging preparation for skin is provided.

In a second technical solution of the present disclosure, an anti-aging preparation for skin is provided, including a 4-[(1E)-2-[[(4-chlorophenyl)methyl]sulfonyl]alkyne]-benzoic acid and/or a salt thereof as components.

In a third technical solution of the present disclosure, an anti-aging composition for skin is provided, including a 4-[(1E)-2-[[(4-chlorophenyl)methyl]sulfonyl]alkyne]-benzoic acid and/or a salt thereof as components.

In a fourth technical solution of the present disclosure, applications of the forgoing anti-aging preparation for skin and anti-aging composition for skin in preparing a drug for promoting the synthesis of type I collagen are provided.

In a fifth technical solution of the present disclosure, applications of the forgoing anti-aging preparation for skin and anti-aging composition for skin in preparing an anti-aging drug, skincare product, cosmetic and cosmeceutical for skin are provided.

In a sixth technical solution of the present disclosure, an anti-aging drug for skin is provided, including a 4-[(1E)-2-[[(4-chlorophenyl)methyl]sulfonyl]alkyne]-benzoic acid and/or a salt thereof as components.

In a seventh technical solution of the present disclosure, a skincare product is provided, including a 4-[(1E)-2-[[(4-chlorophenyl)methyl]sulfonyl]alkyne]-benzoic acid and/or a salt thereof as components.

In an eighth technical solution of the present disclosure, a cosmetic is provided, including a 4-[(1E)-2-[[(4-chlorophenyl)methyl]sulfonyl]alkyne]-benzoic acid and/or a salt thereof as components.

In a ninth technical solution of the present disclosure, a cosmeceutical is provided, including a 4-[(1E)-2-[[(4-chlorophenyl)methyl]sulfonyl]alkyne]-benzoic acid and/or a salt thereof as components.

The present disclosure has the following technical effects.

In the present disclosure, the anti-aging effect of 4-[(1E)-2-[[(4-chlorophenyl)methyl]sulfonyl]alkyne]-benzoic acid and a salt thereof (such as sodium 4-[(1E)-2-[[(4-chlorophenyl)methyl]sulfonyl]alkyne]-benzoate) on skin has been discovered. A series of anti-aging experiments for skin are conducted using sodium 4-[(1E)-2-[[(4-chlorophenyl)methyl]sulfonyl]alkyne]-benzoate as an example in the present disclosure, and the results show that 24-48 h after administration, the sodium 4-[(1E)-2-[[(4-chlorophenyl)methyl]sulfonyl]alkyne]-benzoate has no damage to the primary fibroblasts of mice, and can significantly increase the expression of type I collagen (COL1A2) in the fibroblasts. Applying an aqueous solution of sodium 4-[(1E)-2-[[(4-chlorophenyl)methyl]sulfonyl]alkyne]-benzoate to the hair-removed skin on the backs of mice once a day for 30 consecutive days can significantly downregulate the MMP-13 content in the skin on the backs of mice, increase the expression of COL1A2 and the collagen fiber content in the treated skin, resulting in a thicker dermis of the treated skin and exerting a significant anti-aging effect on skin. And the 4-[(1E)-2-[[(4-chlorophenyl)methyl]sulfonyl]alkyne]-benzoic acid and the salt thereof can be applied in preparing the anti-aging preparation for skin.

BRIEF DESCRIPTION OF THE DRAWINGS

For clearer technical solutions of the examples in the present disclosure or in the prior art, the accompanying drawings required in the examples will be described briefly below. Obviously, the accompanying drawings described below are some examples of the present disclosure. For those ordinary skilled in the art, other drawings can be obtained according to these drawings without creative efforts.

DETAILED DESCRIPTION

Figure 1:
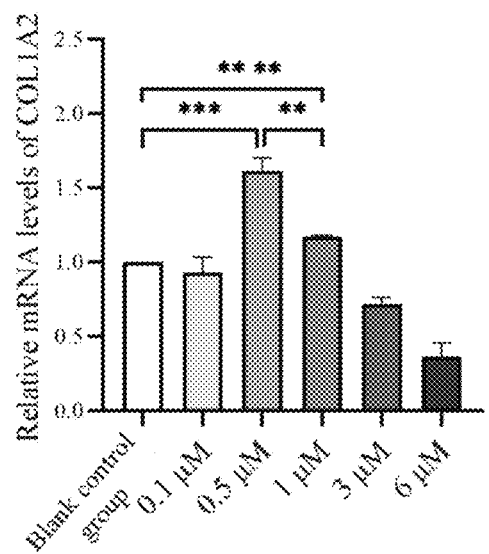
FIG. 1 shows the expression of COL1A2 in fibroblasts after being treated with different concentrations of sodium 4-[(1E)-2-[[(4-chlorophenyl)methyl]sulfonyl]alkyne]-benzoate for 24 h.

Hereinafter, various exemplary embodiments of the present disclosure are described in detail, and this detailed description is not to be construed as limiting the present disclosure, but rather as describing certain aspects, features, and implementations of the present disclosure in more details.

It is to be understood that the term used herein is merely for describing particular embodiments rather than limiting the present disclosure. Additionally, for numerical range mentioned in the present disclosure, it is to be understood that each intermediate value in the upper and lower limits of the range is also specifically disclosed. Intermediate values within any stated values or stated ranges, as well as any smaller ranges in any stated values or any stated intermediate values within the range are also included in the present disclosure. The upper and lower limits of these smaller ranges may independently be included in or excluded from the range.

Unless otherwise specified, all technical and scientific terms used herein have the same meaning as those generally understood by ordinary skilled in the technical field to which the present disclosure belongs. Although only preferred methods and materials are described in the present disclosure, any methods and materials similar or equivalent to those described herein may also be used in the implementation or testing of the present disclosure.

Without departing from the scope or spirit of the present disclosure, various improvements and variations may be made to the specific embodiments of the specification in the present disclosure, which are apparent to those skilled in the art, and other embodiments derived from the specification of the present disclosure will be also apparent to those skilled in the art. The specification and examples of the present disclosure are merely illustrative.

The terms "containing", "including", "having", "comprising," and the like used herein are in the open form, meaning including but not limited to.

The "%" mentioned in the present disclosure, unless otherwise specified, represents mass percentage.

In a first aspect of the present disclosure, an application of a 4-[(1E)-2-[[(4-chlorophenyl)methyl]sulfonyl]alkyne]-benzoic acid and a salt thereof in preparing an anti-aging preparation for skin is provided.

In the present disclosure, a 4-[(1E)-2-[[(4-chlorophenyl)methyl]sulfonyl]alkyne]-benzoic acid salt may be sodium 4-[(1E)-2-[[(4-chlorophenyl)methyl]sulfonyl]alkyne]-benzoate.

Since discovery, 4-[(1E)-2-[[(4-chlorophenyl)methyl]sulfonyl]alkyne]-benzoic acid and sodium 4-[(1E)-2-[[(4-chlorophenyl)methyl]sulfonyl]alkyne]-benzoate (structural formula)

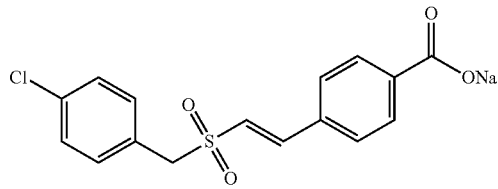

have not been disclosed or implied to have anti-aging and wrinkle-removing effects on skin. In the present disclosure, after repeated and in-depth research, it is the first time to discover that 4-[(1E)-2-[[(4-chlorophenyl)methyl]sulfonyl]alkyne]-benzoic acid and a salt thereof (sodium 4-[(1E)-2-[[(4-chlorophenyl)methyl]sulfonyl]alkyne]-benzoate) have the effect of promoting the synthesis of type I collagen, which, after being added to a drug, a cosmetic, a skincare product, or a cosmeceutical, if applied to skin, can increase the skin elasticity, reduce wrinkles, and realize the anti-aging effect.

In the present disclosure, a series of experiments prove that sodium 4-[(1E)-2-[[(4-chlorophenyl)methyl]sulfonyl]alkyne]-benzoate has no damage to fibroblasts of mice and can promote the expression of COL1A2 in fibroblasts. Applying an aqueous solution of sodium 4-[(1E)-2-[[(4-chlorophenyl)methyl]sulfonyl]alkyne]-benzoate to the hair-removed skin on the backs of mice can downregulate the MMP-13 content in the treated skin, increase the COL1A2 content and the collagen fiber content in the treated skin, resulting in a thicker dermis of the treated skin on the backs of mice.

On the basis of the above studies, the present disclosure provides a new anti-aging preparation for skin containing a 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate. The anti-aging preparation for skin can be prepared by adding the 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate to medically acceptable solvent carriers (such as purified water, glycerin, and mineral fat) for skin anti-aging.

Further, a person skilled in the art can understand that, in view of the anti-aging effect of 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate on skin, the 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate can be easily added into skincare products, cosmeceuticals, or other cosmetics to prepare anti-aging skincare products, cosmeceuticals, or other cosmetics for skin containing 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate.

In addition, a person skilled in the art can understand that, except for being applied in the above-described skincare products, cosmetics and cosmeceuticals, the 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate can be prepared into other pharmaceutically acceptable preparations for therapeutic or cosmetic purposes for skin anti-aging; or the 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate can be prepared into anti-aging compositions for skin with other carriers suitable for topical application to the skin.

In a second aspect of the present disclosure, an anti-aging preparation for skin is provided, including a 4-[(1E)-2-[[(4-chlorophenyl)methyl]sulfonyl]alkyne]-benzoic acid and/or a salt thereof as components.

In the present disclosure, excipients acceptable in the fields of pharmaceutics, or skincare product, cosmetic, and cosmeceutical are included. Specifically, they may be pharmaceutically acceptable carriers and solvents, or additives commonly used in skincare products, cosmetics, or cosmeceuticals, and the like.

In a preferred embodiment of the present disclosure, the content of the 4-[(1E)-2-[[(4-chlorophenyl)methyl]sulfonyl]alkyne]-benzoic acid and/or the salt thereof in the anti-aging preparation for skin is 0.5-1 μM. In a more preferred embodiment of the present disclosure, the content of the 4-[(1E)-2-[[(4-chlorophenyl)methyl]sulfonyl]alkyne]-benzoic acid in the anti-aging preparation for skin is 0.5-1 μM, or, the content of a sodium 4-[(1E)-2-[[(4-chlorophenyl)methyl]sulfonyl]alkyne]-benzoate in the anti-aging preparation for skin is 0.5-1 μM. In a further preferred embodiment of the present disclosure, the content of the 4-[(1E)-2-[[(4-chlorophenyl)methyl]sulfonyl]alkyneene]-benzoic acid in the anti-aging preparation for skin is 0.5 μM, or, the content of the sodium 4-[(1E)-2-[[(4-chlorophenyl)methyl]sulfonyl]alkyne]-benzoate in the anti-aging preparation for skin is 0.5 μM.

In a third aspect of the present disclosure, an anti-aging composition for skin is provided, including a 4-[(1E)-2-[[(4-chlorophenyl)methyl]sulfonyl]alkyne]-benzoic acid and/or a salt thereof as components.

In a preferred embodiment of the present disclosure, the content of the 4-[(1E)-2-[[(4-chlorophenyl)methyl]sulfonyl]alkyne]-benzoic acid and/or the salt thereof in the anti-aging composition for skin is 0.5-1 μM. In a more preferred embodiment of the present disclosure, the content of the 4-[(1E)-2-[[(4-chlorophenyl)methyl]sulfonyl]alkyne]-benzoic acid in the anti-aging composition for skin is 0.5-1 μM, or, the content of a sodium 4-[(1E)-2-[[(4-chlorophenyl)methyl]sulfonyl]alkyne]-benzoate in the anti-aging composition for skin is 0.5-1 μM. In a further preferred embodiment of the present disclosure, the content of the 4-[(1E)-2-[[(4-chlorophenyl)methyl]sulfonyl]alkyneene]-benzoic acid in the anti-aging composition for skin is 0.5 μM, or, the content of the sodium 4-[(1E)-2-[[(4-chlorophenyl)methyl]sulfonyl]alkyne]-benzoate in the anti-aging composition for skin is 0.5 μM.

In a fourth aspect of the present disclosure, applications of the forgoing anti-aging preparation for skin and anti-aging composition for skin in preparing a drug for promoting the synthesis of type I collagen are provided.

In a fifth aspect of the present disclosure, applications of the forgoing anti-aging preparation for skin and anti-aging composition for skin in preparing an anti-aging drug for skin, an anti-aging skincare product for skin, an anti-aging cosmetic for skin and an anti-aging cosmeceutical for skin are provided.

In a sixth aspect of the present disclosure, an anti-aging drug for skin is provided, including a 4-[(1E)-2-[[(4-chlorophenyl)methyl]sulfonyl]alkyne]-benzoic acid and/or a salt thereof as components.

In a preferred embodiment of the present disclosure, the content of the 4-[(1E)-2-[[(4-chlorophenyl)methyl]sulfonyl]alkyne]-benzoic acid and/or the salt thereof in the anti-aging drug for skin is 0.5-1 µM. In a more preferred embodiment of the present disclosure, the content of the 4-[(1E)-2-[[(4-chlorophenyl)methyl]sulfonyl]alkyne]-benzoic acid in the anti-aging drug for skin is 0.5-1 µM, or, the content of a sodium 4-[(1E)-2-[[(4-chlorophenyl)methyl]sulfonyl]alkyne]-benzoate in the anti-aging drug for skin is 0.5-1 µM. In a further preferred embodiment of the present disclosure, the content of the 4-[(1E)-2-[[(4-chlorophenyl)methyl]sulfonyl]alkyne]-benzoic acid in the anti-aging drug for skin is 0.5 µM, or, the content of the sodium 4-[(1E)-2-[[(4-chlorophenyl)methyl]sulfonyl]alkyne]-benzoate in the anti-aging drug for skin is 0.5 µM.

In a seventh aspect of the present disclosure, an anti-aging skincare product for skin is provided, including a 4-[(1E)-2-[[(4-chlorophenyl)methyl]sulfonyl]alkyne]-benzoic acid and/or a salt thereof as components.

In a preferred embodiment of the present disclosure, the content of the 4-[(1E)-2-[[(4-chlorophenyl)methyl]sulfonyl]alkyne]-benzoic acid and/or the salt thereof in the anti-aging skincare product for skin is 0.5-1 µM. In a more preferred embodiment of the present disclosure, the content of the 4-[(1E)-2-[[(4-chlorophenyl)methyl]sulfonyl]alkyne]-benzoic acid in the anti-aging skincare product for skin is 0.5-1 µM, or, the content of a sodium 4-[(1E)-2-[[(4-chlorophenyl)methyl]sulfonyl]alkyne]-benzoate in the anti-aging skincare product for skin is 0.5-1 µM. In a further preferred embodiment of the present disclosure, the content of the 4-[(1E)-2-[[(4-chlorophenyl)methyl]sulfonyl]alkyne]-benzoic acid in the anti-aging skincare product for skin is 0.5 µM, or, the content of the sodium 4-[(1E)-2-[[(4-chlorophenyl)methyl]sulfonyl]alkyne]-benzoate in the anti-aging skincare product for skin is 0.5 µM.

In an eighth aspect of the present disclosure, an anti-aging cosmetic for skin is provided, including a 4-[(1E)-2-[[(4-chlorophenyl)methyl]sulfonyl]alkyne]-benzoic acid and/or a salt thereof as components.

In a preferred embodiment of the present disclosure, the content of the 4-[(1E)-2-[[(4-chlorophenyl)methyl]sulfonyl]alkyne]-benzoic acid and/or the salt thereof in the anti-aging cosmetic for skin is 0.5-1 µM. In a more preferred embodiment of the present disclosure, the content of the 4-[(1E)-2-[[(4-chlorophenyl)methyl]sulfonyl]alkyne]-benzoic acid in the anti-aging cosmetic for skin is 0.5-1 µM, or, the content of a sodium 4-[(1E)-2-[[(4-chlorophenyl)methyl]sulfonyl]alkyne]-benzoate in the anti-aging cosmetic for skin is 0.5-1 µM. In a further preferred embodiment of the present disclosure, the content of the 4-[(1E)-2-[[(4-chlorophenyl)methyl]sulfonyl]alkyne]-benzoic acid in the anti-aging cosmetic for skin is 0.5 µM, or, the content of the sodium 4-[(1E)-2-[[(4-chlorophenyl)methyl]sulfonyl]alkyne]-benzoate in the anti-aging cosmetic for skin is 0.5 µM.

In a ninth aspect of the present disclosure, an anti-aging cosmeceutical for skin is provided, including a 4-[(1E)-2-[[(4-chlorophenyl)methyl]sulfonyl]alkyne]-benzoic acid and/or a salt thereof as components.

In a preferred embodiment of the present disclosure, the content of the 4-[(1E)-2-[[(4-chlorophenyl)methyl]sulfonyl]alkyne]-benzoic acid and/or the salt thereof in the anti-aging cosmeceutical for skin is 0.5-1 µM. In a more preferred embodiment of the present disclosure, the content of the 4-[(1E)-2-[[(4-chlorophenyl)methyl]sulfonyl]alkyne]-benzoic acid in the anti-aging cosmeceutical for skin is 0.5-1 µM, or, the content of a sodium 4-[(1E)-2-[[(4-chlorophenyl)methyl]sulfonyl]alkyne]-benzoate in the anti-aging cosmeceutical for skin is 0.5-1 µM. In a further preferred embodiment of the present disclosure, the content of the 4-[(1E)-2-[[(4-chlorophenyl)methyl]sulfonyl]alkyne]-benzoic acid in the anti-aging cosmeceutical for skin is 0.5 µM, or, the content of the sodium 4-[(1E)-2-[[(4-chlorophenyl)methyl]sulfonyl]alkyne]-benzoate in the anti-aging cosmeceutical for skin is 0.5 µM.

In the following examples, experiments for the anti-aging effect on skin are conducted using sodium 4-[(1E)-2-[[(4-chlorophenyl)methyl]sulfonyl]alkyne]-benzoate as an example. The sodium 4-[(1E)-2-[[(4-chlorophenyl)methyl]sulfonyl]alkyne]-benzoate has the following structural formula:

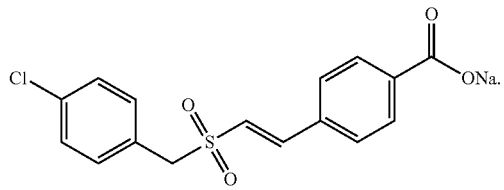

Example 1

The anti-aging effect of sodium 4-[(1E)-2-[[(4-chlorophenyl)methyl]sulfonyl]alkyne]-benzoate on skin (1) Culture of Mouse Skin Fibroblasts Experimental method: skin tissues were taken from the backs of newborn C57BL/6 mice, and fibroblasts obtained from mice were isolated and purified. The fibroblasts were cultured in a dulbecco's modified eagle medium (DMEM)/F12 medium (hereinafter referred to as "normal medium") containing 10% (volume fraction) of superior fetal bovine serum (FBS) and 1% (volume fraction) of penicillin-streptomycin, followed by culturing in a 37° C. incubator with 5% (volume fraction) $CO_2$. The third-generation of fibroblasts were taken for experiments.

(2) Determination of Appropriate Drug Concentration

Experimental method: the COL1A2 level was detected using fluorescent quantitative polymerase chain reaction (PCR) method. The experiment was divided into two major groups: a blank control group and a sodium 4-[(1E)-2-[[(4-chlorophenyl)methyl]sulfonyl]alkyne]-benzoate treatment group. In the blank control group, the fibroblasts were cultured in a normal medium; and in the sodium 4-[(1E)-2-[[(4-chlorophenyl)methyl]sulfonyl]alkyne]-benzoate treatment group, the fibroblasts were treated with five media containing different concentrations (0.1 µM, 0.5 M, 1 µM, 3

μM, and 6 μM) of sodium 4-[(1E)-2-[[(4-chlorophenyl) methyl]sulfonyl]alkyne]-benzoate (i.e., normal medium added with sodium 4-[(1E)-2-[[(4-chlorophenyl)methyl] sulfonyl]alkyne]-benzoate at the aforementioned concentrations) for 24 h. The specific process was as follows. The third-generation of fibroblasts was uniformly inoculated into a six-well plate. In the blank control group, the fibroblasts were cultured in the normal medium, and in the sodium 4-[(1E)-2-[[(4-chlorophenyl)methyl]sulfonyl]alkyne]-benzoate treatment group, the fibroblasts were cultured in media containing sodium 4-[(1E)-2-[[(4-chlorophenyl)methyl] sulfonyl]alkyne]-benzoate at the corresponding concentrations. After 24 h of culture, total RNA was extracted from the fibroblasts and subjected to reverse transcription to obtain complementary deoxyribonucleic acid (cDNA), which was then subjected to fluorescent quantitative PCR. After the end of reaction, an amplification curve and a melting curve of the fluorescent quantitative PCR were confirmed, with glyceraldehyde-3-phosphate dehydrogenase (GAPDH) as an internal reference gene. The results were analyzed using the internationally accepted $2^{-\Delta\Delta Ct}$ method.

Total RNA of fibroblasts was extracted using standard laboratory RNA extraction method and stored at −80° C. for later use. The extracted total RNA of fibroblasts was used as a template to synthesize cDNA by using the standard laboratory method, and the synthesized cDNA was stored at −20° C. for later use.

Fluorescent quantitative PCR system: 10 μL of qPCR SYBR Green Master Mix, 2 μL of 2 μM upstream primer, 2 μL of 2 μM downstream primer, and 1000 ng of cDNA template, a total volume of 20 μL by supplementing with diethyl pyrocarbonate (DEPC)-treated water. The upstream and downstream primers are listed in Table 1.

Reaction conditions: pre-denaturation at 95° C. for 5 min, followed by 40 cycles of 10 sec at 95° C., 20 sec at 52.9° C., and 20 sec at 72° C. After the end of reaction, the melting curve was analyzed.

TABLE 1

Fluorescent quantitative PCR amplification primers

| Gene name | | Primer sequence |
|---|---|---|
| COL1A2 | Upstream (5'-3') | GACAAATGAATGGGCAAG |
| | Downstream (5'-3') | CAATGTCCAGAGGTGCAATG |
| GAPDH | Upstream (5'-3') | TGGCCTTCCGTGTTCCTAC |
| | Downstream (5'-3') | GAGTTGCTGTTGAAGTCGCA |

Results: as shown in FIG. 1, after the fibroblasts are treated with sodium 4-[(1E)-2-[[(4-chlorophenyl)methyl] sulfonyl]alkyne]-benzoate at a concentration of 0.5 μM for 24 h, the expression of COL1A2 in the fibroblasts is 1.613 times that of the blank control group (0 μM group), with a statistically significant difference compared to the blank control group (P=0.0003). After the fibroblasts are treated with 1 μM of sodium 4-[(1E)-2-[[(4-chlorophenyl)methyl] sulfonyl]alkyne]-benzoate for 24 h, the expression of COL1A2 in the fibroblasts is 1.173 times that of the blank control group, showing a lower increase than the 0.5 μM of sodium 4-[(1E)-2-[[(4-chlorophenyl)methyl]sulfonyl] alkyne]-benzoate treatment group, with a statistical difference compared to the blank control group (P<0.0001). The treatment of fibroblasts with any other concentrations of sodium 4-[(1E)-2-[[(4-chlorophenyl)methyl]sulfonyl] alkyne]-benzoate cannot increase the expression of COL1A2 in the fibroblasts, suggesting that the treatment with 0.5-1 μM of sodium 4-[(1E)-2-[[(4-chlorophenyl) methyl]sulfonyl]alkyne]-benzoate can increase the expression of COL1A2 in fibroblasts, with 0.5 μM being better than 1 μM.

(3) Determination of Appropriate Administration Frequency

Experimental method: the COL1A2 level was detected using fluorescent quantitative PCR method. The experiment was divided into two major groups: a blank control group and a sodium 4-[(1E)-2-[[(4-chlorophenyl)methyl]sulfonyl] alkyne]-benzoate treatment group. In the blank control group, the fibroblasts were cultured in a normal medium; and in the sodium 4-[(1E)-2-[[(4-chlorophenyl)methyl] sulfonyl]alkyne]-benzoate treatment group, the fibroblasts were cultured in a medium containing 0.5 μM of sodium 4-[(1E)-2-[[(4-chlorophenyl)methyl]sulfonyl]alkyne]-benzoate, with incubation times of 24 h, 48 h, and 72 h. The specific process was as follows. The third-generation of fibroblasts was uniformly inoculated into a six-well plate. In the blank control group, the fibroblasts were cultured in a normal medium, and in the sodium 4-[(1E)-2-[[(4-chlorophenyl)methyl]sulfonyl]alkyne]-benzoate treatment group, the fibroblasts were cultured in a medium containing 0.5 μM of sodium 4-[(1E)-2-[[(4-chlorophenyl)methyl]sulfonyl] alkyne]-benzoate (i.e., normal medium containing 0.5μ M of sodium 4-[(1E)-2-[[(4-chlorophenyl)methyl]sulfonyl] alkyne]-benzoate). After culturing for 24 h, 48 h, and 72 h, total RNA was extracted from the fibroblasts and subjected to reverse transcription to obtain cDNA, which was then subjected to fluorescent quantitative PCR. After the end of reaction, an amplification curve and a melting curve of the fluorescent quantitative PCR were confirmed, with GAPDH as an internal reference gene. The results were analyzed using the internationally accepted $2^{-\Delta\Delta Ct}$ method.

The method for extracting total RNA of fibroblasts, the method for synthesizing cDNA, the fluorescent quantitative PCR system, the reaction conditions, and the upstream and downstream primer sequences were all the same as those described in "(2) of Example 1".

Figure 2:
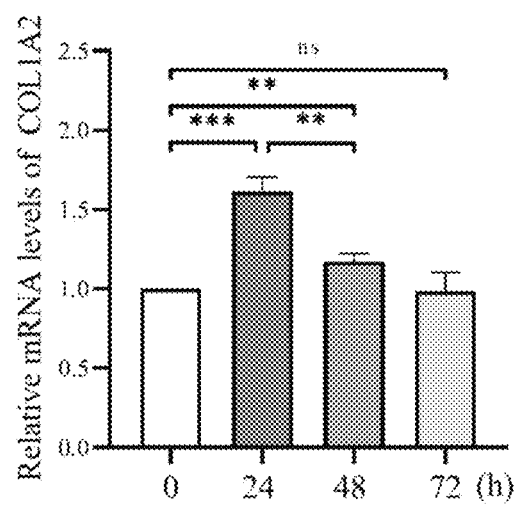
FIG. 2 shows the effect of sodium 4-[(1E)-2-[[(4-chlorophenyl)methyl]sulfonyl]alkyne]-benzoate at a concentration of 0.5 µM at different incubation times on the expression of COL1A2 in fibroblasts.

Results: as shown in FIG. 2, with the extension of incubation time from 24 h to 72 h, the expression of COL1A2 in fibroblasts decreases. At the incubation time of 72 h, there is no difference in the expression of COL1A2 in fibroblasts compared to the blank control group, suggesting that an administration frequency of once every 24-48 h is appropriate, with once every 24 h being optimal.

(4) Detection of Cell Viability after Administration

Experimental method: the third-generation of fibroblasts was uniformly inoculated into a six-well plate. In the blank control group, the fibroblasts were cultured in a normal medium, and in the sodium 4-[(1E)-2-[[(4-chlorophenyl) methyl]sulfonyl]alkyne]-benzoate treatment group, the fibroblasts were cultured in a medium containing 0.5 μM of sodium 4-[(1E)-2-[[(4-chlorophenyl)methyl]sulfonyl] alkyne]-benzoate (i.e., normal medium containing 0.5 μM of sodium 4-[(1E)-2-[[(4-chlorophenyl)methyl]sulfonyl] alkyne]-benzoate). After culturing for 24 h and 48 h, respectively, the status of fibroblasts was photographed under a microscope.

Figure 3:
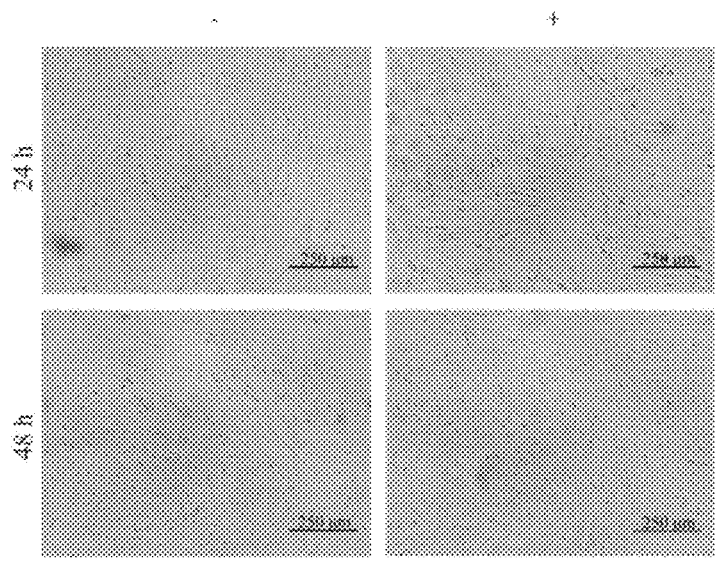
FIG. 3 shows the effect of sodium 4-[(1E)-2-[[(4-chlorophenyl)methyl]sulfonyl]alkyne]-benzoate at a concentration of 0.5 µM on the viability of fibroblasts.

Results: as shown in FIG. 3, "−" represents the blank control group, and "+" represents the sodium 4-[(1E)-2-[[(4-chlorophenyl)methyl]sulfonyl]alkyne]-benzoate treatment group. After the fibroblasts with 0.5 of are treated sodium 4-[(1E)-2-[[(4-chlorophenyl)methyl]sulfonyl]alkyne]-benzoate for 24 h and 48 h, there is no obvious and visual changes in the status of fibroblasts, suggesting that 0.5 μM of sodium 4-[(1E)-2-[[(4-chlorophenyl)methyl]sulfonyl]alkyne]-benzoate has no adverse effects on viability of fibroblasts.

Example 2

Anti-aging preparation for skin containing sodium 4-[(1E)-2-[[(4-chlorophenyl)methyl]sulfonyl]alkyne]-benzoate Sodium 4-[(1E)-2-[[(4-chlorophenyl)methyl]sulfonyl]alkyne]-benzoate was dissolved in water to prepare an aqueous solution of sodium 4-[(1E)-2-[[(4-chlorophenyl)methyl]sulfonyl]alkyne]-benzoate (i.e., an anti-aging preparation for skin). Six healthy C57BL/6 mice aged 6-8 weeks with similar body sizes were selected, and the hair on the backs of the mice was removed gently and harmlessly to expose a similar area of skin on the back of each mouse. The six mice were divided into two groups equally. The same volume of pure water and aqueous solutions containing 0.5 of sodium 4-[(1E)-2-[[(4-chlorophenyl)methyl]sulfonyl]alkyne]-benzoate were applied, respectively, to the hair-removed skin on the backs of the mice once a day for 30 consecutive days.

(1) Detection of COL1A2 Content in Skin

Experimental method: after continuously applying the same volume of aqueous solutions containing 0.5 μM of sodium 4-[(1E)-2-[[(4-chlorophenyl)methyl]sulfonyl]alkyne]-benzoate or pure water as a blank control to the backs of mice for 30 days, the mice were euthanized for cutting the skin from the treated areas. The Westernblot method was employed to detect the protein level of COL1A2, and the fluorescent quantitative PCR method was employed to detect the mRNA level of COL1A2.

The specific process for the Westernblot experiment was as follows. Total protein was extracted from skin tissues, and an equal mass of the collected protein samples were loaded into wells of a sodium dodecyl sulfate polyacrylamide gel electrophoresis (SDS-PAGE) gel, followed by electrophoresis, transmembrane, blocking, and incubation of primary antibodies (COL1A2 antibody and GAPDH antibody). After fluorescent secondary antibodies were incubated, the samples were visualized using an infrared fluorescence scanning imaging system. The visualized images were analyzed for grayscale of band using Image J software on a gel imaging system, and the relative expression of the target protein was calculated using internal reference protein GAPDH as correction.

Figure 4A:
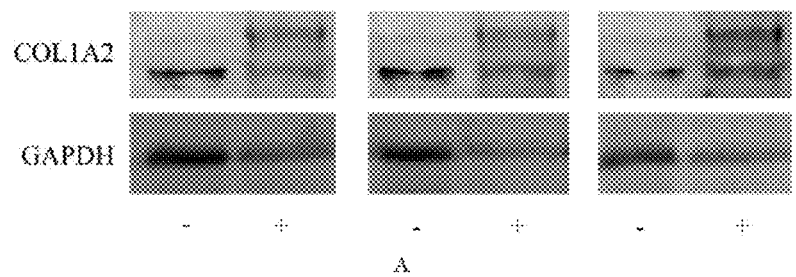
FIG. 4A is gel images showing the effect of an aqueous solution of sodium 4-[(1E)-2-[[(4-chlorophenyl)methyl]sulfonyl]alkyne]-benzoate on the protein content of COL1A2 in skin.
Figure 4B:
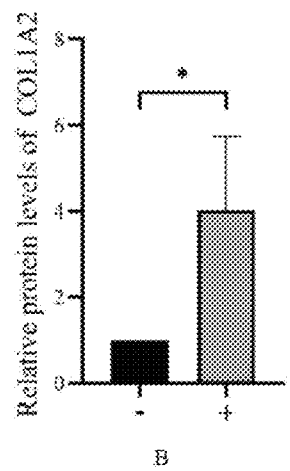
FIG. 4B is a quantitative analysis bar graph showing the effect of an aqueous solution of sodium 4-[(1E)-2-[[(4-chlorophenyl)methyl]sulfonyl]alkyne]-benzoate on the protein content of COL1A2 in skin.

Results: as shown in FIG. 4A and FIG. 4B, FIG. 4A shows gel images, and FIG. 4B shows a quantitative analysis bar graph. "−" represents the pure water blank control group, and "+" represents the aqueous solution of sodium 4-[(1E)-2-[[(4-chlorophenyl)methyl]sulfonyl]alkyne]-benzoate treatment group. Compared to the pure water blank control group, the protein level of COL1A2 in the aqueous solution of sodium 4-[(1E)-2-[[(4-chlorophenyl)methyl]sulfonyl]alkyne]-benzoate treatment group increases by 4.024 times, with a statistical difference compared to the pure water blank control group (P=0.0378), suggesting that applying the aqueous solution of sodium 4-[(1E)-2-[[(4-chlorophenyl)methyl]sulfonyl]alkyne]-benzoate to skin can increase the protein content of COL1A2 in the skin.

Fluorescence quantitative PCR experiment was performed specifically as follows. Total RNA was extracted from skin tissues, and subjected to reverse transcription to obtain cDNA, which was then subjected to fluorescence quantitative PCR. After the end of reaction, an amplification curve and a melting curve of the fluorescent quantitative PCR were confirmed, with GAPDH as an internal reference gene. The results were analyzed using the internationally accepted $2^{-\Delta\Delta Ct}$ method.

Total RNA of tissues was extracted using standard laboratory RNA extraction method and stored at −80° C. for later use. The extracted total RNA of tissues was used as a template to synthesize cDNA by using the standard laboratory method, and the synthesized cDNA was stored at −20° C. for later use.

The fluorescence quantitative PCR system, the upstream and downstream primers, and the reaction conditions were the same as those in "(2) of Example 1".

Figure 5:
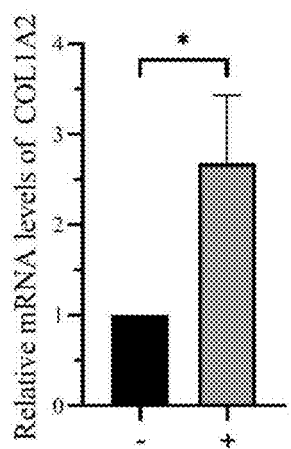
FIG. 5 shows the effect of an aqueous solution of sodium 4-[(1E)-2-[[(4-chlorophenyl)methyl]sulfonyl]alkyne]-benzoate on the messenger ribonucleic acid (mRNA) content of COL1A2 in skin.

Results: as shown in FIG. 5, "−" represents the pure water blank control group, and "+" represents the aqueous solution of sodium 4-[(1E)-2-[[(4-chlorophenyl)methyl]sulfonyl]alkyne]-benzoate treatment group. Compared to the pure water blank control group, the mRNA level of COL1A2 in the aqueous solution of sodium 4-[(1E)-2-[[(4-chlorophenyl)methyl]sulfonyl]alkyne]-benzoate treatment group increases by 2.681 times, with a statistical difference compared to the pure water blank control group (P=0.0178), suggesting that applying the aqueous solution of sodium 4-[(1E)-2-[[(4-chlorophenyl)methyl]sulfonyl]alkyne]-benzoate to skin can increase the mRNA content of COL1A2 in the skin.

(2) Detection of Collagen Fiber Content in Skin

Experimental method: after continuously applying an aqueous solution containing 0.5 μM of sodium 4-[(1E)-2-[[(4-chlorophenyl)methyl]sulfonyl]alkyne]-benzoate or pure water as a blank control to the backs of mice for 30 days, the mice were euthanized for cutting the skin from the treated areas, and the Masson staining method was used for detecting the collagen fiber content in the skin. Specifically, tissues were fixed, dehydrated with a sucrose solution, embedded in an optimal cutting temperature (OCT), sliced, stained with hematoxylin, differentiated with acidic ethanol, counterstained blue with a Masson's blueing solution, stained with a Ponceau-Fuchsin staining solution, stained with an aniline blue staining solution, rinsed with a weak acid working solution, dehydrated with 95% ethanol (volume fraction), dehydrated with absolute ethanol, cleared with xylene, and mounted with neutral gum.

Figure 6A:
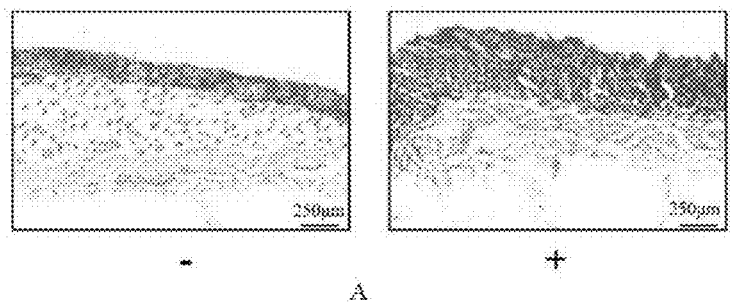
FIG. 6A is staining result images showing the effect of an aqueous solution of sodium 4-[(1E)-2-[[(4-chlorophenyl)methyl]sulfonyl]alkyne]-benzoate on the collagen fiber content in skin.
Figure 6B:
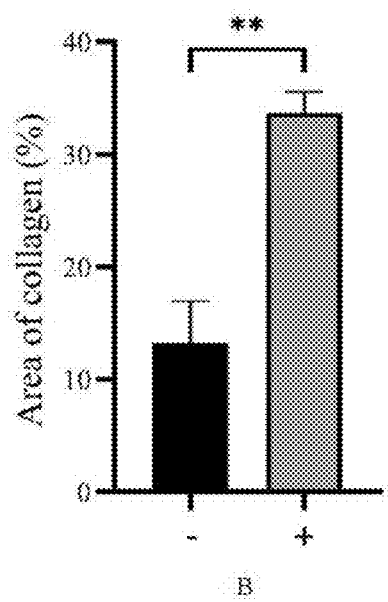
FIG. 6B is a quantitative analysis bar graph showing the effect of an aqueous solution of sodium 4-[(1E)-2-[[(4-chlorophenyl)methyl]sulfonyl]alkyne]-benzoate on the collagen fiber content in skin.

Results: as shown in FIG. 6A and FIG. 6B, FIG. 6A shows staining result images; and FIG. 6B is a quantitative analysis bar graph. "−" represents the pure water blank control group, and "+" represents the aqueous solution of sodium 4-[(1E)-2-[[(4-chlorophenyl)methyl]sulfonyl]alkyne]-benzoate treatment group. Compared to the pure water blank control group, the collagen fiber content in the skin of the aqueous solution of sodium 4-[(1E)-2-[[(4-chlorophenyl)methyl]sulfonyl]alkyne]-benzoate treatment group increases by 3.3904 times, with a statistical difference compared to the pure water blank control group (P=0.0010), suggesting that applying the aqueous solution of sodium 4-[(1E)-2-[[(4-chlorophenyl)methyl]sulfonyl]alkyne]-benzoate to skin can increase the collagen fiber content in the skin.

(3) Detection of Dermal Thickness in Skin

Experimental method: after continuously applying an aqueous solution containing 0.5 μM of sodium 4-[(1E)-2-[[(4-chlorophenyl)methyl]sulfonyl]alkyne]-benzoate or pure water as a blank control to the backs of mice for 30 days, the mice were euthanized for cutting the skin from the treated areas, and hematoxylin-eosin (HE) staining method was used for detecting the dermal thickness in the skin. Specifically, the tissues were fixed, dehydrated with a sucrose solution, embedded in OCT, sliced, stained with hematoxylin, counterstained blue with tap water, stained with eosin, dehydrated and cleared, and then mounted.

Figure 7A:
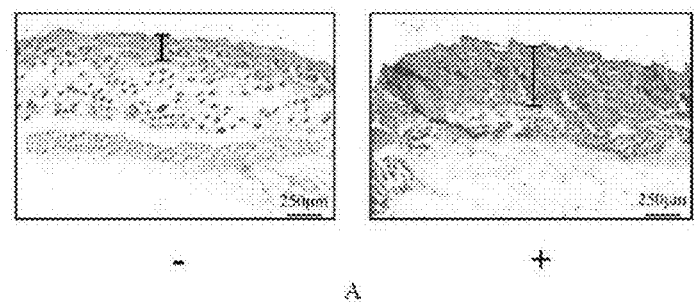
FIG. 7A is staining result images showing the effect of an aqueous solution of sodium 4-[(1E)-2-[[(4-chlorophenyl)methyl]sulfonyl]alkyne]-benzoate on the dermal thickness in skin.
Figure 7B:
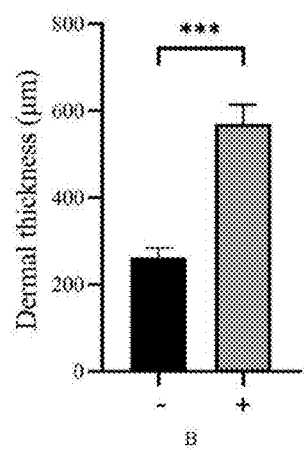
FIG. 7B is a quantitative analysis bar graph showing the effect of an aqueous solution of sodium 4-[(1E)-2-[[(4-chlorophenyl)methyl]sulfonyl]alkyne]-benzoate on the dermal thickness in skin.

Results: as shown in FIG. 7A and FIG. 7B, FIG. 7A shows staining result images, where the range marked by the line segments represents the range of dermal thickness; and FIG. 7B is a quantitative analysis bar graph. "–" represents the pure water blank control group, and "+" represents the aqueous solution of sodium 4-[(1E)-2-[[(4-chlorophenyl)methyl]sulfonyl]alkyne]-benzoate treatment group. Compared to the pure water blank control group, the dermal thickness in the skin of the aqueous solution of sodium 4-[(1E)-2-[[(4-chlorophenyl)methyl]sulfonyl]alkyne]-benzoate treatment group increases by 2.9101 times, with a statistical difference compared to the pure water blank control group (P=0.0004), suggesting that applying the aqueous solution of sodium 4-[(1E)-2-[[(4-chlorophenyl)methyl]sulfonyl]alkyne]-benzoate to skin can increase the dermal thickness in the skin.

(4) Detection of MMP-13 Content in Skin

Experimental method: after continuously applying an aqueous solution containing 0.5 M of sodium 4-[(1E)-2-[[(4-chlorophenyl)methyl]sulfonyl]alkyne]-benzoate or pure water as a blank control to the backs of mice for 30 days, the mice were euthanized for cutting the skin from the treated areas, and the fluorescent quantitative PCR method was used for detecting the mRNA level of MMP-13 in skin tissue. Specifically, total RNA was extracted from skin tissues, and subjected to reverse transcription to obtain cDNA, which was then subjected to fluorescence quantitative PCR. After the end of reaction, an amplification curve and a melting curve of the fluorescent quantitative PCR were confirmed, with GAPDH as an internal reference gene. The results were analyzed using the internationally accepted $2^{-\Delta\Delta Ct}$ method.

Total RNA of tissues was extracted using standard laboratory RNA extraction method and stored at −80° C. for later use. The extracted total RNA of tissue was used as a template to synthesize cDNA by using the standard laboratory method, and the synthesized cDNA was stored at −20° C. for later use.

Fluorescent quantitative PCR system: 10 μL of qPCR SYBR Green Master Mix, 2 μL of 2 μM upstream primer, 2 μL of 2 μM downstream primer, and 1000 ng of cDNA template, a total volume of 20 μL by supplementing with DEPC-treated water. The upstream and downstream primers are listed in Table 2.

Reaction conditions: pre-denaturation at 95° C. for 5 min, followed by 40 cycles of 10 sec at 95° C., 20 sec at 55.7° C., and 20 sec at 72° C. After the end of reaction, the melting curve was analyzed.

TABLE 2

Fluorescent quantitative PCR amplification primers

| Gene name | | Primer sequence |
|---|---|---|
| MMP-13 | Upstream (5'-3') | CTTCTTCTTGTTGAGCTGGACTC (SEQ ID NO. 1) |
| | Downstream (5'-3') | CTGTGGAGGTCACTGTAGACT (SEQ ID NO. 2) |
| GAPDH | Upstream (5'-3') | TGGCCTTCCGTGTTCCTAC (SEQ ID NO. 3) |
| | Downstream (5'-3') | GAGTTGCTGTTGAAGTCGCA (SEQ ID NO. 4) |

Figure 8:
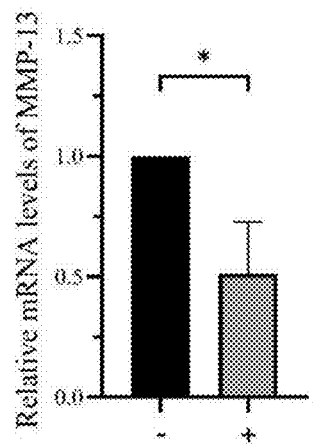
FIG. 8 shows the effect of an aqueous solution of sodium 4-[(1E)-2-[[(4-chlorophenyl)methyl]sulfonyl]alkyne]-benzoate on the MMP-13 content in skin.

Results: as shown in FIG. 8, "–" represents the pure water blank control group, and "+" represents the aqueous solution of sodium 4-[(1E)-2-[[(4-chlorophenyl)methyl]sulfonyl]alkyne]-benzoate treatment group. Compared to the pure water blank control group, the mRNA level of MMP-13 in the aqueous solution of sodium 4-[(1E)-2-[[(4-chlorophenyl)methyl]sulfonyl]alkyne]-benzoate treatment group decreases by 0.5124 times, with a statistical difference compared to the pure water blank control group (P=0.0171), suggesting that applying the aqueous solution of sodium 4-[(1E)-2-[[(4-chlorophenyl)methyl]sulfonyl]alkyne]-benzoate to skin can decrease the MMP-13 content in the skin.

It can be seen that long-term application of preparations containing sodium 4-[(1E)-2-[[(4-chlorophenyl)methyl]sulfonyl]alkyne]-benzoate can decrease the clinical symptoms of skin aging, increase the collagen fiber content and the dermal thickness in the skin, lighten wrinkles, and make the skin firmer and more delicate.

In the present disclosure, the 4-[(1E)-2-[[(4-chlorophenyl)methyl]sulfonyl]alkyne]-benzoic acid underwent the same effect verification as sodium 4-[(1E)-2-[[(4-chlorophenyl)methyl]sulfonyl]alkyne]-benzoate in the aforementioned Examples 1 and 2. The results show that 4-[(1E)-2-[[(4-chlorophenyl)methyl]sulfonyl]alkyne]-benzoic acid has equivalent effects to the sodium 4-[(1E)-2-[[(4-chlorophenyl)methyl]sulfonyl]alkyne]-benzoate in increasing the expression of type I collagen (COL1A2) in cells, and the collagen fiber content and the dermal thickness in the skin.

It is to be noted that a person skilled in the art can understand that, in view of the anti-aging effect of 4-[(1E)-2-[[(4-chlorophenyl)methyl]sulfonyl]alkyne]-benzoic acid and sodium 4-[(1E)-2-[[(4-chlorophenyl)methyl]sulfonyl]alkyne]-benzoate on skin, the 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate can be easily added into skincare products, cosmeceuticals, or other cosmetics to prepare anti-aging skincare products, cosmeceuticals, or other cosmetics for skin containing 4-[(1E)-2-[[(4-chlorophenyl)methyl]sulfonyl]alkyne]-benzoic acid and/or sodium 4-[(1E)-2-[[(4-chlorophenyl)methyl]sulfonyl]alkyne]-benzoate.

In this example, the sodium 4-[(1E)-2-[[(4-chlorophenyl)methyl]sulfonyl]alkyne]-benzoate is prepared into an aqueous solution, which has a good anti-aging effect on skin. Those skilled in the art can understand that the dosage forms of the aforementioned solvents, carriers, or 4-[(1E)-2-[[(4-chlorophenyl)methyl]sulfonyl]alkyne]-benzoic acid (or the salt thereof, such as sodium salt and potassium salt, which will all dissociate

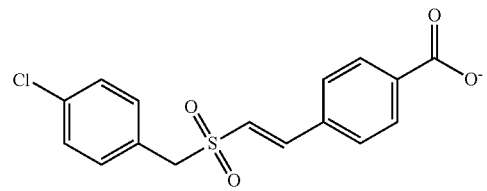 [SMILES: O=C([O-])c1ccc(/C=C/S(=O)(=O)Cc2ccc(Cl)cc2)cc1]

in solution, and this is the main component for the anti-aging effect on skin; and therefore, 4-[(1E)-2-[[(4-chlorophenyl)methyl]sulfonyl]alkyne]-benzoic acid and the salt thereof can achieve the same anti-aging effect) are not intended to limit the present disclosure. Those skilled can mix the 4-[(1E)-2-[[(4-chlorophenyl)methyl]sulfonyl]alkyne]-benzoic acid and/or the salt thereof with moisturizing components such as glycerin, butylene glycol, and sodium hyaluronate to prepare an anti-aging moisturizer for skin. They can also mix the 4-[(1E)-2-[[(4-chlorophenyl)methyl]sulfonyl]alkyne]-benzoic acid and/or the salt thereof with emulsifiers such as stearyl alcohol and glyceryl stearate to prepare a lightweight, stable and sprayable oil-in-water anti-aging emulsion for skin. Furthermore, they can mix the 4-[(1E)-2-[[(4-chlorophenyl)methyl]sulfonyl]alkyne]-benzoic acid and/or the salt thereof with emulsifiers such as PEG-20 methyl glucose sesquistearate and steareth-21 to prepare a thicker oil-in-water anti-aging cream for skin. In addition, without departing from the basic concept of the present disclosure, multiple compositions containing 4-[(1E)-2-[[(4-chlorophenyl)methyl]sulfonyl]alkyne]-benzoic acid and/or the salt thereof can be prepared, and as long as the composition is used in beauty or therapeutic treatments for skin anti-aging, it falls within the scope of protection of the present disclosure.

The above-mentioned examples are merely used for describing the preferred embodiment of the present disclosure, rather than limiting the scope of the present disclosure. Without departing from the design spirit of the present disclosure, various modifications and improvements made by those ordinary skilled in the art to the technical solutions of the present disclosure are included in the protection scope defined by the claims of the present disclosure.

The invention claimed is:

1. A method for using a 4-[(1E)-2-[[(4-chlorophenyl)methyl]sulfonyl]alkyne]-benzoic acid and a salt thereof in an anti-aging preparation for skin, comprising:

adding the 4-[(1E)-2-[[(4-chlorophenyl)methyl]sulfonyl]alkyne]-benzoic acid and the salt thereof to a medically acceptable solvent carrier to obtain the anti-aging preparation for skin, wherein content of the 4-[(1E)-2-[[(4-chlorophenyl)methyl]sulfonyl]alkyne]-benzoic acid and/or the salt thereof in the anti-aging preparation for skin is 0.5-1 µM.

2. A method for using an anti-aging preparation for skin in a drug promoting the synthesis of type I collagen, comprising:

adding the anti-aging preparation for skin as a component to prepare the drug promoting the synthesis of type I collagen, wherein components of the anti-aging preparation for skin comprises a 4-[(1E)-2-[[(4-chlorophenyl)methyl]sulfonyl]alkyne]-benzoic acid and/or a salt thereof; and content of the 4-[(1E)-2-[[(4-chlorophenyl)methyl]sulfonyl]alkyne]-benzoic acid and/or the salt thereof in the anti-aging preparation for skin is 0.5-1 µM.

* * * * *

```
                        SEQUENCE LISTING

Sequence total quantity: 4
SEQ ID NO: 1            moltype = DNA  length = 23
FEATURE                 Location/Qualifiers
source                  1..23
                        mol_type = other DNA
                        organism = synthetic construct
SEQUENCE: 1
cttcttcttg ttgagctgga ctc                                              23

SEQ ID NO: 2            moltype = DNA  length = 21
FEATURE                 Location/Qualifiers
source                  1..21
                        mol_type = other DNA
                        organism = synthetic construct
SEQUENCE: 2
ctgtggaggt cactgtagac t                                                21

SEQ ID NO: 3            moltype = DNA  length = 19
FEATURE                 Location/Qualifiers
source                  1..19
                        mol_type = other DNA
                        organism = synthetic construct
SEQUENCE: 3
tggccttccg tgttcctac                                                   19

SEQ ID NO: 4            moltype = DNA  length = 20
FEATURE                 Location/Qualifiers
source                  1..20
                        mol_type = other DNA
                        organism = synthetic construct
SEQUENCE: 4
gagttgctgt tgaagtcgca                                                  20
```